United States Patent
Kondo et al.

(10) Patent No.: US 7,358,650 B2
(45) Date of Patent: Apr. 15, 2008

(54) ULTRASOUND PROBE (75) Inventors: Toshiro Kondo, Sanuki (JP); Takaya Osawa, Saitama (JP)

(73) Assignee: Hitachi Medical Corporation, Tokyo (JP)

( * ) Notice: Subject to any disclaimer, the term of this patent is extended or adjusted under 35 U.S.C. 154(b) by 0 days.

(21) Appl. No.: 10/547,378
(22) PCT Filed: Feb. 27, 2004
(86) PCT No.: PCT/JP2004/002387

§ 371 (c)(1),
(2), (4) Date: Jun. 12, 2006

(87) PCT Pub. No.: WO2004/075753

PCT Pub. Date: Sep. 10, 2004

(65) Prior Publication Data
US 2006/0232164 A1 Oct. 19, 2006

(30) Foreign Application Priority Data
Feb. 27, 2003 (JP) ............................. 2003-052038

(51) Int. Cl.
H04R 17/00 (2006.01)
(52) U.S. Cl. ...................................... 310/334; 600/459
(58) Field of Classification Search ................ 310/334, 310/326–327; 600/459, 437
See application file for complete search history.

(56) References Cited

U.S. PATENT DOCUMENTS

| 5,251,490 A | * | 10/1993 | Kronberg ................. 73/861.25 |
| 7,084,552 B2 | * | 8/2006 | Bhardwaj ................... 310/327 |
| 2001/0021807 A1 | * | 9/2001 | Saito et al. ................. 600/437 |
| 2005/0122004 A1 | * | 6/2005 | Shibamoto et al. ......... 310/334 |
| 2006/0079785 A1 | * | 4/2006 | Hosono et al. ............. 600/459 |

FOREIGN PATENT DOCUMENTS

| JP | 1-119199 | 5/1989 |
| JP | 7-284198 | 10/1995 |
| JP | 10-56694 | 2/1998 |
| JP | 10-75953 | 3/1998 |
| JP | 2001-309495 | 11/2001 |
| JP | 2002-247696 | 8/2002 |

* cited by examiner

*Primary Examiner*—J. San Martin
(74) *Attorney, Agent, or Firm*—Antonelli, Terry, Stout & Kraus, LLP

(57) ABSTRACT

An ultrasound probe obtained by arranging, on a backing 10, a plurality of transducers each of which comprising a piezoelectric transducer 20, an acoustic lens 40, and an acoustic matching layer provided between the piezoelectric transducer 20 and the acoustic lens 40, the acoustic matching layer containing a fibrous material, and the direction of fibers in the fibrous material being perpendicular to the direction of sound waves.

14 Claims, 6 Drawing Sheets

32 ACOUSTIC MATCHING LAYER
31 ACOUSTIC MATCHING LAYER
20 PIEZOELECTRIC TRANSDUCER
10 BACKING MATERIAL (SOUND ABSORBING MATERIAL)

Fig. 5

61 ACOUSTIC MATCHING LAYER, ULTRA-HIGH MOLECULAR WEIGHT POLYETHYLENE COMPOSITE MATERIAL
62 ACOUSTIC MATCHING LAYER, CARBON FIBER COMPOSITE MATERIAL
20 PIEZOELECTRIC TRANSDUCER
10 BACKING MATERIAL (SOUND ABSORBING MATERIAL)

DIRECTION OF PROPAGATION OF SOUND WAVES

ULTRASOUND PROBE

TECHNICAL FIELD

This invention relates to a probe in an ultrasound diagnostic apparatus and, particularly, to a transducer in an electronic scanning probe.

BACKGROUND ART

A probe in an electronic scanning ultrasonic diagnostic apparatus that transmits and receives ultrasonic waves has heretofore been constituted by arranging, on a backing material, a plurality of transducers each of which comprising a piezoelectric transducer, an acoustic lens, and an acoustic matching layer provided between the piezoelectric transducer and the acoustic lens.

In this probe, a transducer of a narrow width having the acoustic matching layer vibrates accompanied, however, by a deformation in the direction of thickness, by a deformation in the direction of width and, hence, by a reduction in the conversion efficiency in the direction of thickness. Further, since the vibration in the direction of width interferes with the vibration in the direction of thickness, the surface of the transducer goes out of vibration of a uniform amplitude deteriorating the image of the ultrasonic diagnostic equipment.

A probe obtained by arranging the vibrators that have a fibrous material dispersed in the acoustic matching layer has been disclosed in JP-A-10-75953. However, this fibrous material is used for realizing a low heat conduction, and the direction of fiber has not been set by taking the Young's modulus of the fiber and the Poisson's ratio into consideration. Therefore, the above problem cannot be solved by the above prior art.

DISCLOSURE OF THE INVENTION

This invention is concerned with an ultrasound probe obtained by arranging, on a backing, a plurality of transducers each of which comprising a piezoelectric transducer, an acoustic lens, and an acoustic matching layer provided between the piezoelectric transducer and the acoustic lens, the acoustic matching layer containing a fibrous material, and the direction of fibers in the fibrous material being perpendicular to the direction of sound waves.

BEST MODE FOR CARRYING OUT THE INVENTION

Figure 1:
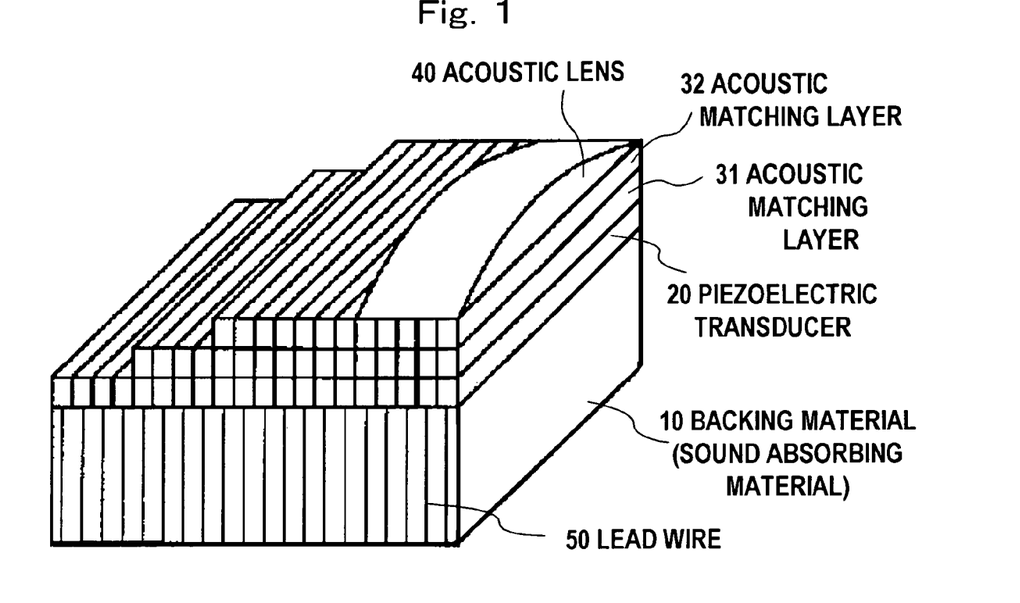
FIG. 1 is a view illustrating the internal structure of an ultrasound probe according to the present invention.

Referring to FIG. 1, there are arranged many slender and rod-like piezoelectric transducers 20 having a narrow width made of PZT on a sound-absorbing (backing) material 10, which are covered with an acoustic lens 40 of a shape arcuately swelling outward in a direction at right angles with the direction of arrangement thereof and with an acoustic matching layer 31 and an acoustic matching layer 32 that are provided between the transducers 20 and the acoustic lens 40. Lead wires 50 are connected to the electrodes of the vibrators.

The PZT has been extensively used as a piezoelectric transducer of the ultrasonic probe. Acoustic impedances of the PZT and the living body or water of $Z_0=35\times 10^6$ [kg/m$^2\cdot$s] and $Z_M=1.5\times 10^6$ [kg/m$^2\cdot$s], respectively. There is a large difference between these values. From the standpoint of impedance matching, the matching cannot be quite accomplished if the PZT is brought into contact with the living body. Therefore, the acoustic matching layers 31 and 32 are provided on the front surface of the transducer to bring the acoustic impedance of the transducer 20 into match with the acoustic impedance of the living body. This enables the vibration of the transducer 20 to be efficiently propagated into the living body.

The epoxy and the polyurethane used for the acoustic matching layers 31 and 32 have acoustic impedances of 2 to 3 [MRayl]. Since the living body has an acoustic impedance of 1.5 [MRayl], it is most desired to use the epoxy or the polyurethane on the upper surface of the acoustic matching layer of the two-layer constitution. As the lower layer of the acoustic matching layer, it is necessary to use a material having an acoustic impedance lying between that of the vibrator and that of the upper layer of the acoustic matching layer. Therefore, a powder of a substance having a relatively large density is mixed into the epoxy or polyurethane resin to adjust the value that meets the lower surface of the acoustic matching layer.

The reflection coefficient R on the interface between the PZT and the living body is given by the formula (1) like the case of an electric circuit, $$R = \left|\frac{Z_M - Z_0}{Z_M + Z_0}\right| \tag{1}$$

Figure 2:
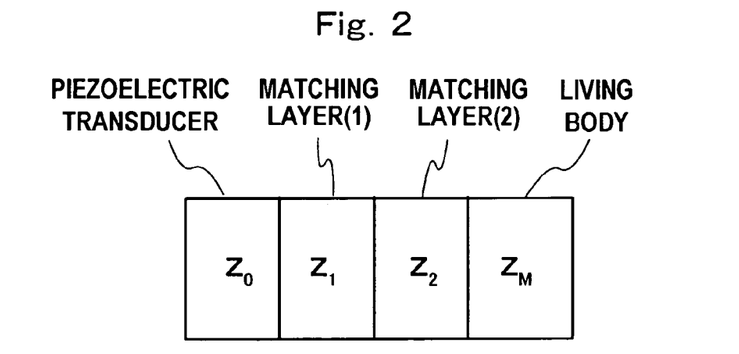
FIG. 2 is a diagram illustrating a propagation model of sound waves of the probe.
Figure 3:
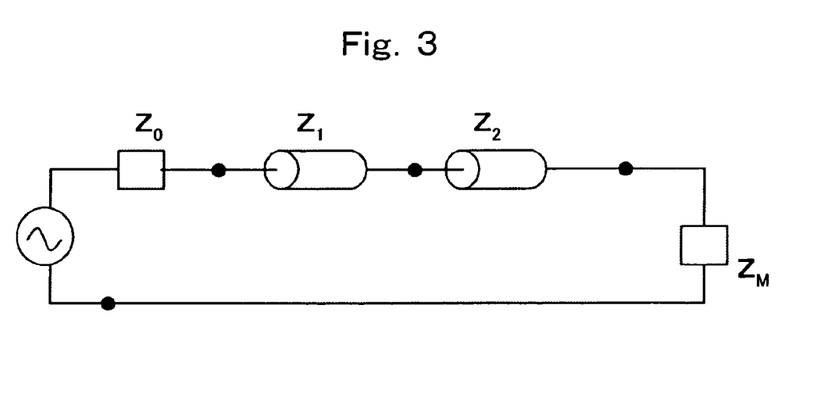
FIG. 3 is a diagram illustrating a model of an equivalent circuit of a passage through which the sound waves propagate from the piezoelectric transducer in the probe to the human body.

In an electric circuit, it is a practice to insert a $\lambda/4$ matching circuit in the circuit. Here, $\lambda$ is a wavelength of signals that propagate. A matching layer for propagating ultrasonic waves of the probe will now be considered based on a model shown in FIG. 2. FIG. 3 shows its equivalent circuit. $Z_0$, $Z_1$, $Z_2$ and $Z_M$ denote acoustic impedances of the piezoelectric vibrator, the matching layer (1), the matching layer (2) and the human body.

$Z_0$ and $Z_M$ have been given. Optimum values of characteristic impedances $Z_1$ and $Z_2$ can be determined by calculation by using a coaxial cable put between a signal source and a receiving end to minimize the reflection at the terminals of the coaxial cable having characteristic impedances $Z_1$ and $Z_2$ ("REVISED HANDBOOK OF ULTRASONIC EQUIPMENT FOR MEDICAL USE" compiled by the, Foundation, Japanese Industrial Association of Electronic Machines, published by Corona Co., Jan. 20, 1997, pp. 29-30). Table 1 shows optimum acoustic impedances of the acoustic matching layer of a thickness of ¼ wavelength.

TABLE 1

Optimum acoustic impedances of ¼ wavelength acoustic matching layer.

| Acoustic impedance of piezoelectric vibrator | Acoustic impedance $Z_i$ of matching layer | | | | | Acoustic impedance $Z_M$ of human body |
|---|---|---|---|---|---|---|
| | 1 | 2 | 3 | 4 | 5 | |
| 34 | 4.25 | / | / | / | / | 1.5 |
| | 8.92 | 2.34 | / | / | / | |
| | 14.79 | 4.24 | 1.85 | / | / | |
| | 20.55 | 7.51 | 2.74 | 1.66 | / | |
| | 25.26 | 12.01 | 4.46 | 2.12 | 1.58 | |

(Note):
Unit is all by ×10 [kg/m² · s]

An optimum method of designing the probe using the equivalent circuit is based on a wave equation of sound waves by taking into consideration only the sound waves that propagate in the longitudinal direction. It is presumed that no deformation in the transverse direction occurs in the matching layer.

The backing material 10 is provided on the back surface of the ultrasound transducer, so that ultrasonic waves coming out from the back surface will not return back to the surface of the transducer, and is made of a material which attenuates the ultrasonic waves to a large degree.

Figure 4:
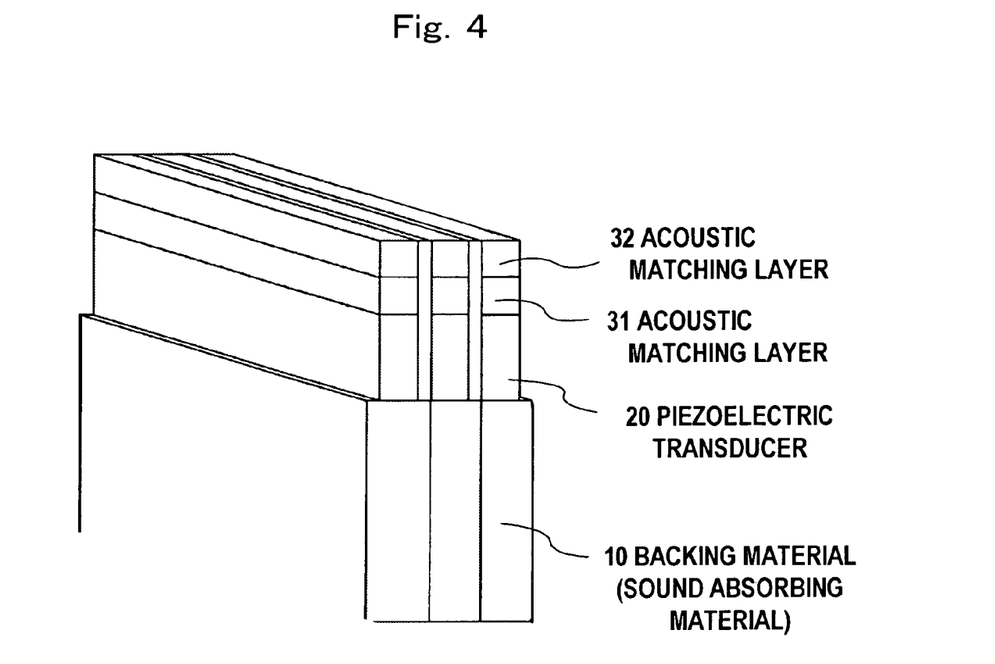
FIG. 4 is a view illustrating, in detail, the internal structure of an ultrasound probe according to the invention.

FIG. 4 is a view illustrating the probe in detail. The piezoelectric transducer 20 exists on the backing member 10, and the acoustic matching layers 31, 32 are provided on the piezoelectric transducer 20. There exists a small gap among the vibrators which are each constituted by the piezoelectric transducer 20, acoustic matching layers 31, 32, and acoustic lens.

Figure 5:
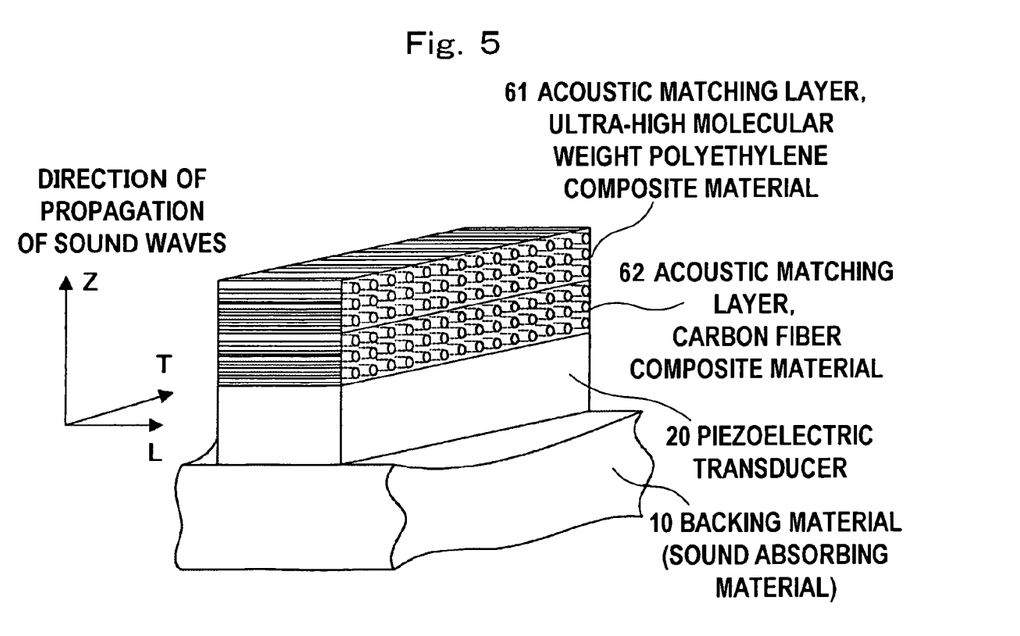
FIG. 5 is a view illustrating a first embodiment of the invention.

Here, described below in detail as a first embodiment is the structure of a probe using a composite material as the matching layers. FIG. 5 illustrates a transducer in this probe. The transducer is constituted by two matching layers and a piezoelectric transducer. A fibrous material is contained in the two matching layers. The direction of fibers of the fibrous material is perpendicular to the direction of propagation of sound waves and is, further, perpendicular to the lengthwise direction of the transducer. The transducers of this structure are arranged in many number on the backing material 10 thereby to constitute an array-type probe. Concretely, the matching layer 61 uses a composite material of a carbon fiber and an epoxy base matirial which contains a tungsten powder. The matching layer 62 uses a composite material of a polyurethane base material and an ultrahigh molecular weight polyethylene fiber. The composite material used for either of these matching layers have densities and Young's moduli in a direction in which the ultrasonic waves propagate, which can be adjusted to be nearly the same as those of the base materials and, hence, their acoustic impedances can be adjusted to assume nearly the same values. The Young's moduli become very large values in the direction of fiber contributing greatly to improving the characteristics of the probe.

Figure 6A:
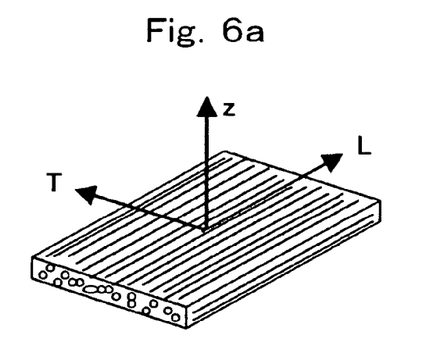
FIGS. 6a and 6b are views illustrating the characteristics of a composite material including a fibrous material of the invention.

Next, described below in detail are the contents of the matching layers. FIG. 6(a) is a one-direction reinforcing plate obtained by arranging the fibers in the same direction. This material is symmetrical on the LZ plane, on the TZ plane or on the LT plane. Here, the axes L, T and Z are referred to as anisotropic main axes (elastic main axes, principal axes) which in FIG. 6(a) are referred to as orthotropy in which the main axes are meeting each other at right angles.

Figure 6B:
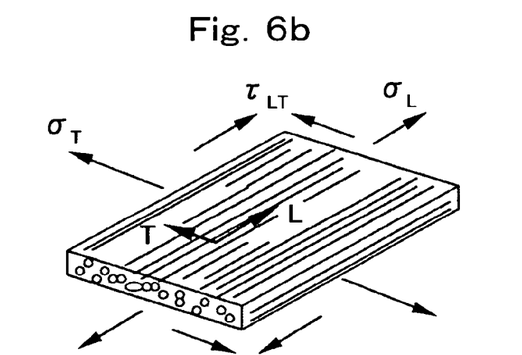

When a stress $\sigma_L$ is exerted in a direction L in FIG. 6(b), the strain are given by the formulas (2), $$\varepsilon_T = \frac{v_{LT}\sigma_L}{E_L}, \varepsilon_L = \frac{\sigma_T}{E_L} \tag{2}$$

where $E_L$ is a Young's modulus when pulled in the direction L, and $v_{LT}$ is a Poisson's ratio representing the ratio of contraction in the direction T when pulled in the direction L. Similarly, when a stress $\sigma_T$ is exerted in the direction T in FIG. 6(b), the strain are given by the formulas (3), $$\varepsilon_T = \frac{\sigma_T}{E_T}, \varepsilon_L = -\frac{v_{TL}\sigma_T}{E_T} \tag{3}$$

On the other hand, a relationship of the formula (4) holds between the shearing stress and the shearing strain, $$\gamma_{LT} = \frac{\tau_{LT}}{G_{LT}} \tag{4}$$

Therefore, when a combined stress acts as shown in FIG. 6(b), a relationship between the stress and the strain can be expressed by a matrix of the formula (5), $$\begin{Bmatrix} \varepsilon_L \\ \varepsilon_T \\ \gamma_{LT} \end{Bmatrix} = \begin{bmatrix} \frac{1}{E_L} & -\frac{v_{TL}}{E_T} & 0 \\ -\frac{v_{LT}}{E_L} & \frac{1}{E_T} & 0 \\ 0 & 0 & \frac{1}{G_{LT}} \end{bmatrix} \begin{Bmatrix} \sigma_L \\ \sigma_T \\ \tau_{LT} \end{Bmatrix} \tag{5}$$

This is the Hooke's law of an ortho-anisotropic thin plate related to the axes LT.

The isotropic material has two independent elastic constants, but there are appearing five constants $E_L$, $E_T$, $v_{LT}$, $v_{TL}$ and $G_{LT}$ in the formula (5). However, a relationship of the formula (6) called (Betti) reciprocal theorem has been theoretically verified, and the ortho-anisotropic thin plate has four independent elastic constants.

$$\frac{v_{LT}}{E_l} = \frac{v_{TL}}{E_T} \tag{6}$$

These are called basic elastic constants. The elastic constants can be estimated to some extent from the properties of the fibers and the base materials, and are derived from a model that is considered as described below.

Figure 7:
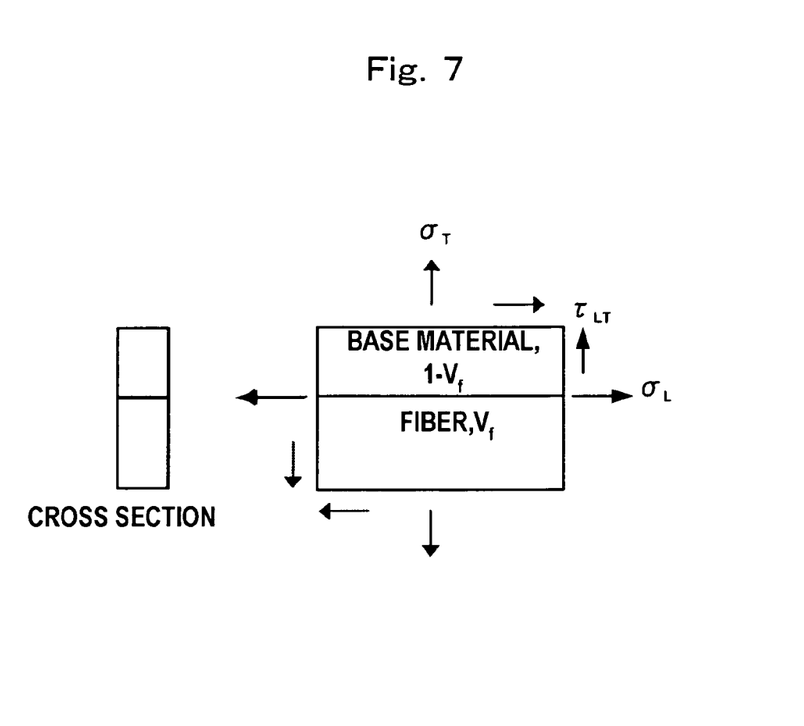
FIG. 7 is a diagram illustrating the characteristics of a composite material including the fibrous material of the invention.

The fiber usually has a circular shape in cross section and is surrounded by the base material. Here, as shown in FIG. 7, the fiber and the base material are collected separately. When pulled in the direction L, this material is elongated like when a bundle of springs that elongate little and springs that elongate much is pulled, and the following formula (7) will be derived as a result of simple calculation, $$E_L = E_f V_f + E_m (1-V_f) \quad (7)$$

where $E_f$ and $E_m$ are Young's moduli of the fiber and the mother member, and $V_f$ is a volume content of the fiber.

The fiber and the mother member arranged in parallel in the direction L are called parallel model which is shown in FIG. 7.

Next, when pulled in the direction T in FIG. 6, the material becomes analogous to the connection of a strong spring of the length $V_f$ and a weak spring of the length $(1-V_f)$ as expressed by the formula (8), $$\frac{1}{E_T} = \frac{V_f}{E_f} + \frac{1-V_f}{E_m} \quad (8)$$

Based upon the idea of the above series and parallel models, the Poisson's ratio $v_{LT}$ and the shearing elastic coefficient $G_{LT}$ can be found from the formulas (9) and (10), $$v_{LT} = v_f V_f + v_m (1 - V_f) \quad (9)$$

$$\frac{1}{G_{LT}} = \frac{V_f}{G_f} + \frac{1-V_f}{G_m} \quad (10)$$

The above idea is called a strength-of-material method in the microscopic elasticity. The above formula (7) is called the composite rule (of modulus of elasticity)(M. Domoto, R, Yamamoto, "Composite Materials", published by the University of Tokyo, Apr. 15, 1993, pp. 39-45).

Tables 3 and 4 show physical properties of the carbon fiber and of an ultrahigh molecular weight polyethylene fiber used for a composite material (a catalogue of carbon fibers of Toyo Rayon Co., material No. 2, revised 17.4.1, and Dieniema catalog A1703K of Toyo Boseki Co.).

TABLE 3

Examples Properties of a carbon fiber.

| Name | | Tensile modulus of elasticity | | Fiber dia. | Density |
|---|---|---|---|---|---|
| | Grade | Tonf/mm² | Gpa | Filament Dia. Micrometer | Density g/cm³ |
| HTA | –W05K | 24.0 | 235 | 7.0 | 1.76 |
| IM600 | –6K | 29.0 | 285 | 5.0 | 1.80 |
| UM46 | –12K | 44.5 | 435 | 4.7 | 1.82 |
| UM68 | –12K | 66.0 | 650 | 4.1 | 1.97 |

TABLE 4

Physical properties of an ultrahigh molecular weight polyethylene fiber.

| Grade | Mod. of elasticity | | Filament dia. | Density |
|---|---|---|---|---|
| | (cN/dtex) | (Gpa) | (μm) | (g/cm3) |
| SK60 | 880-1230 | 88-123 | 12 | 0.97 |
| SK71 | 1230- | 123- | 12 | 0.97 |

Table 5 shows physical properties of an epoxy resin used as the mother member (Asahi Amidas Co./"Plastics" Compiling Dpt., "Plastics Data Book", published by Kogyo Chosakai Publishing Co., Dec. 1, 1999, p. 267).

TABLE 5

Mechanical properties of a bisphenol epoxy resin cured with various curing agents.

| | Composition | Liquid epoxy resin (epoxy equivalent: 180-190) | | |
|---|---|---|---|---|
| Properties | Standards | Polyamine | Amine adduct | Polyamide |
| Specific gravity (kg/cm³) | VSM77109 | 1.15-1.20 | 1.15-1.20 | 1.1-1.2 |
| Mod. of elasticity (kg/mm²) | VSM77111 | 350-400 | 350-400 | 340-390 |
| [Gpa] | | [3.43-3.92] | [3.43-3.92] | [3.33-3.82] |

Araldite GY250 of Chiba Co. was used.

The polyurethane used for the matching layers has a tensile modulus of elasticity of 0.88 [kgf/mm$^2$]. The carbon fiber or the ultrahigh molecular weight polyethylene has a modulus of elasticity (Young's modulus) which is different by at least not less than 22 times from that of the epoxy resin or the polyurethane used as the mother member. The carbon fiber having the greatest modulus of elasticity is different by about 200 times from the modulus of elasticity of the epoxy resin. The kind of the fiber can be arbitrarily selected by the manufacturer depending upon the use.

In an ordinary composite material, the content of the fiber is up to 50% (H. Morimoto, "Plastic Frontier Composite Materials", published by Kobunshi Kankokai, Oct. 5, 1998, pp. 133-134).

In the formula (7), therefore, if it is presumed that $V_f$=0.6, there holds $E_f/E_m$>20 to 200 as described above, from which it is considered that $E_f$>>$E_m$. In the composite material, therefore, the approximation can be made such that, $$E_L \approx E_f E_f \quad (11)$$

It can therefore be so considered that $E_L$ is almost dependent upon the physical properties of the fiber. From the formula (8), on the other hand, $E_T$ can be given by the following formula, $$E_T = \frac{1}{\frac{V_f}{E_f} + \frac{1-V_f}{E_m}} \quad (12)$$

In the formula (12), too, $V_f$=0.2 to 0.4 and $E_f$>>$E_m$ and, hence, there holds $V_f/E_f$<<$(1-V_f/E_m)$. Therefore, $E_T$ is given by the formula (13), $$E_T \approx \frac{E_m}{(1-V_f)} \quad (13)$$

It can therefore be so considered that $E_T$ is almost dependent upon the physical properties of the base material.

From the formula (6), the Poisson's ratio $v_{TL}$ that represents the ratio of elongation of the composite material in the direction of fiber (direction L) by compressing it in the direction (direction T) perpendicular to the direction of fiber is given by the following formula (14), $$v_{TL} = v_{LT} \frac{E_T}{E_L} \quad (14)$$

where $v_{LT}$ is the Poisson's ratio of the composite material of when it is compressed in the direction of fiber. In a typical carbon fiber composite material as shown in Table 6, $v_{LT}$=0.3 (H. Morimoto, "Frontier Composite Materials", published by Kobunshi Kankokai (Kyoto), Oct. 5, 1998, p. 135).

TABLE 6

Compressive modulus of elasticity, Poisson's ratio and density[21] of the carbon fiber composite materials depending upon the kind of carbon fibers.

| | Standard type | Highly strong type | Highly elastic type | Ultra-highly elastic type |
|---|---|---|---|---|
| Compressive modulus of elasticity, 0° C., kgf/mm$^2$ (Gpa) | 15400 (152) | 14700 (145) | 17430 (172) | 31.5 (314) |
| Poisson's ratio | 0.3 | 0.3 | 0.27 | 0.3 |
| Density g/cm$^3$ | 1.58 | 1.61 | 1.59 | 1.83 |

(Note)
[1] Constitution: CF/epoxy(60 to 65 vol %) H. Morimoto: Frontier Composite Material, Kobunshi Kankokai (Kyoto) 1998, p. 135
[2] Kind: Tensile modulus of elasticity of carbon fiber
Standard type (23100 to 23800 kgf/mm$^2$)
Highly strong type (24500 to 31500 kgf/mm$^2$)
Highly elastic type (35000 to 38500 kgf/mm$^2$)

From Table 3, further, the Young's modulus $E_L$ of the composite material may be $E_L$=150 to 300 [GPa]. If it is considered that ET is close to the Young's modulus of the epoxy resin of the mother member, then, $E_T \approx 6$ [GPa] from Table 4. Therefore, $v_{TL}$=0.3×(6/150) to 0.3×(6/300)=0.012 to 0.006 which is a very small value.

Next, the carbon fiber composite material is studied, and, by similarly making reference to Tables 3 and 4, the composite material of the ultrahigh molecular weight polyethylene fiber and the base material of polyurethane also yields the values of $v_{LT}$=0.45, $E_T \approx 1$ [GPa], $E_L$=120 [GPa] and $v_{TL}$v0.45×(1/120) 0.0038 which is a very small value.

Figure 8A:
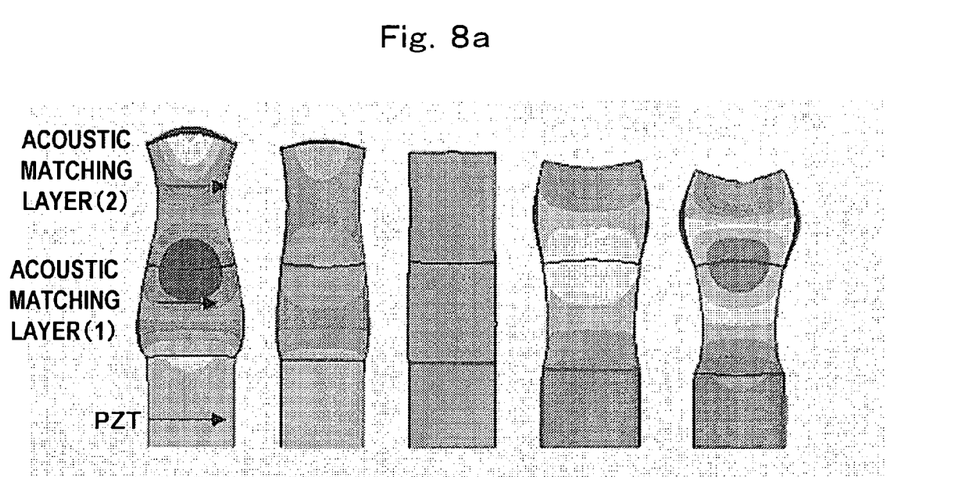
FIGS. 8a and 8b are diagrams illustrating the effect of the invention.
Figure 8B:
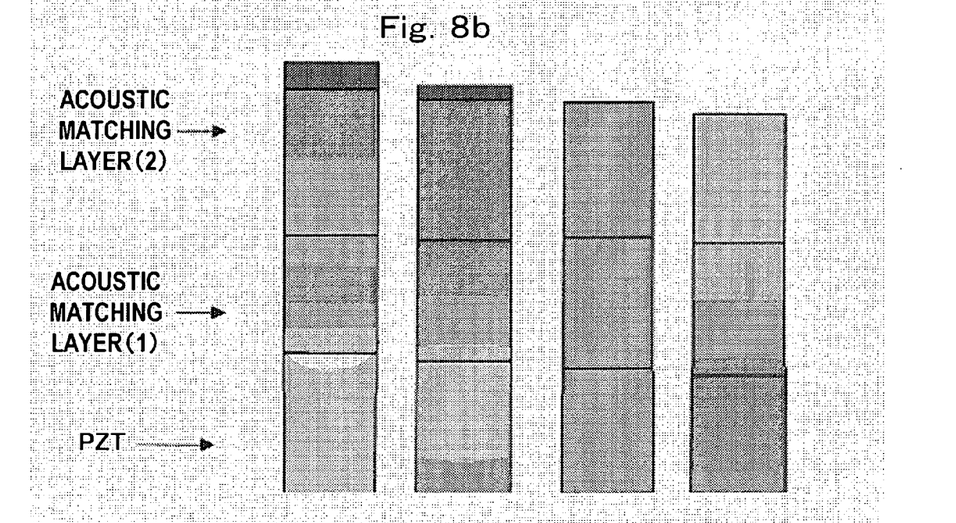

In the conventional matching layer without using the fibrous material as shown in FIG. 8a, the sound waves propagate in a direction perpendicular to the direction of propagation of the sound waves. In this embodiment, on the other hand, the matching layer provided in the vibrator of the array-type probe is constituted of an ortho-anisotropic material in which the sound wave properties in a direction perpendicular to the direction of propagation of sound waves are greatly different from the sound wave properties in the direction of travel of sound waves. As shown in FIG. 8b, therefore, the acoustic impedance can be matched in the direction of propagation of sound waves, and the sound waves propagating in a direction perpendicular to the direction of travel is not coupled by the vibration in the transverse direction of the transducer. Namely, the acoustic matching layer is deformed chiefly in the direction of thickness, and the conversion efficiency can be improved in the direction of thickness. Further, the vibration in the direction of width is prevented from interfering with the vibration in the direction of thickness, and the surface of the vibrator vibrates maintaining a uniform amplitude, making it possible to improve the quality of the image of an ultrasonic diagnostic apparatus.

Next, described below is a method of producing the matching layer. First, the bundle-like fibrous material is roll-pressed and is elongated. At the time of elongating the fibrous material, a resin such as an epoxy or a polyurethane is poured into the fibrous material. The resin infiltrates among the fibers, and a plate-like composite material without space or gap is constituted as shown in FIG. 5. The plate-like composite material is overlapped on the piezoelectric vibrator and the backing material, and is adhered thereto. The laminated composite material is cut maintaining a predetermined distance by using a wire saw or the like.

Further, the fibrous material and the resin are mixed together in advance, and the mixed material is pushed into a plate having a plurality of holes perforated therein permitting the passage of the fibrous material. The fibrous material in the mixed material pushed therein passes through the holes like rods. The fibrous material that has passed through is buried in a resin on the opposite side of the plate and is solidified therein. The plate-like composite material is overlapped on the piezoelectric vibrator and the backing material, and is adhered thereto. The thus laminated composite material is cut maintaining a predetermined distance by using a wire saw or the like. The transducer shown in FIG. 5 is produced by the above-mentioned production method.

Figure 9:
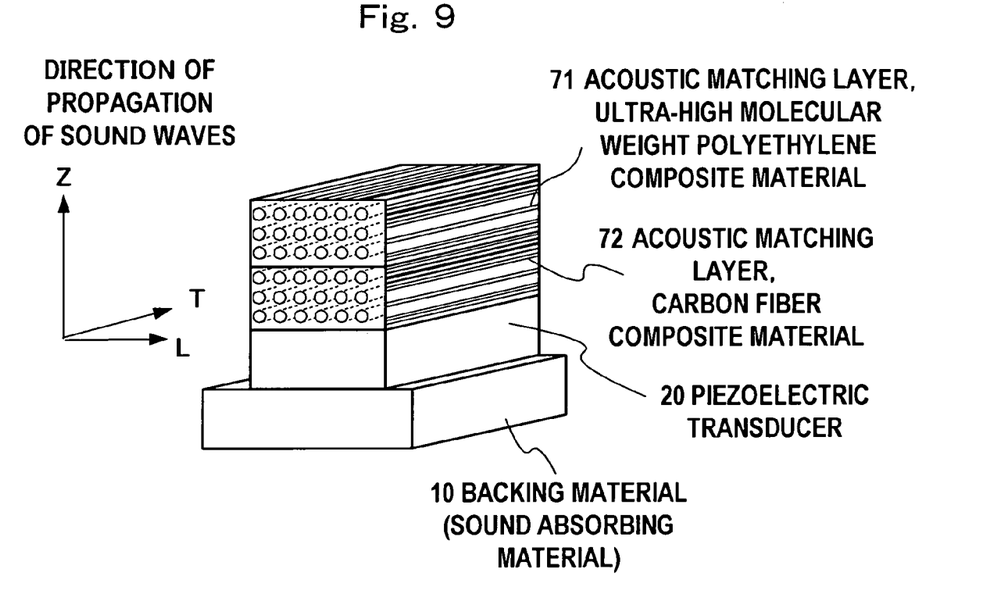
FIG. 9 is a view illustrating a second embodiment of the invention.

Next, described below in detail as a second embodiment is the structure of the probe using the composite material as the, matching layers. FIG. 9 illustrates a transducer in this probe. A fibrous material is contained in the two matching layers. What makes a difference from the first embodiment is that the direction of fibers of the fibrous material in the matching layers 71, 72 is perpendicular to the direction of propagation of sound waves and is in parallel with the lengthwise direction of the transducer. Upon setting the direction of fibers to be in the lengthwise direction of the transducer, the length of the fibers can be lengthened. In this embodiment, therefore, the strength increases in the lengthwise direction.

Figure 10:
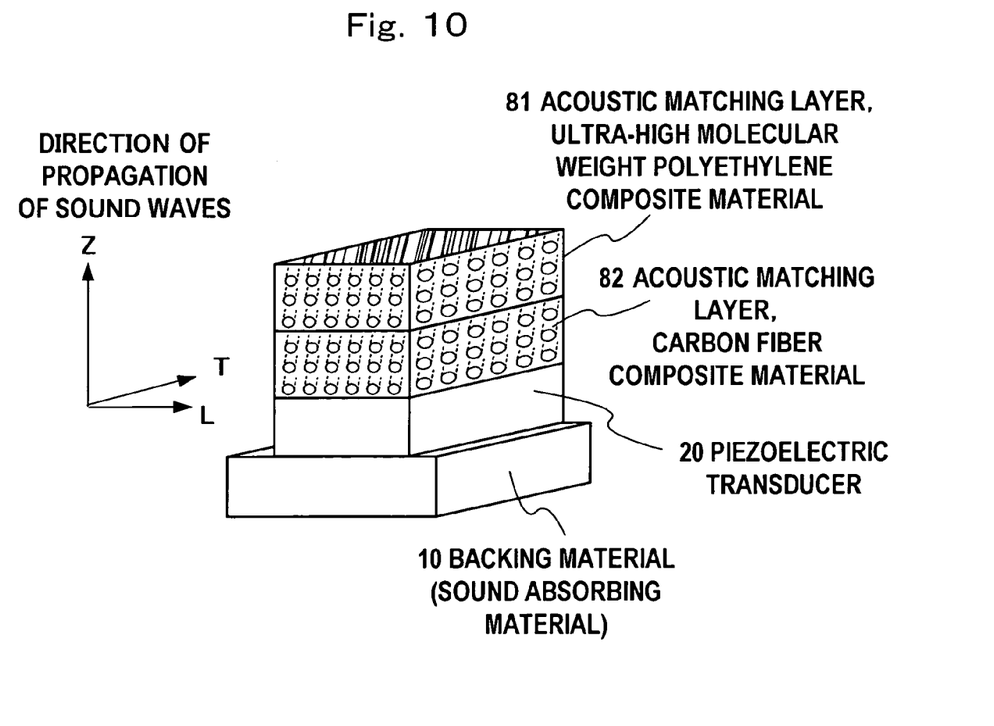
FIG. 10 is a view illustrating a third embodiment of the invention.

Next, described below in detail as a third embodiment is the structure of the probe using the composite material as the matching layers. FIG. 10 illustrates a transducer in this probe. A fibrous material is contained in the two matching layers. What makes a difference from the first and second embodiments is that the direction of fiber of the fibrous material in the matching layers 81, 82 is perpendicular to the direction of propagation of sound waves and is aslant in the lengthwise direction of the transducer. Upon setting the direction of fibers of the matching layers to be aslant in the lengthwise direction of the transducer, the strength increases in both the short-axis direction and the lengthwise direction.

Figure 11:
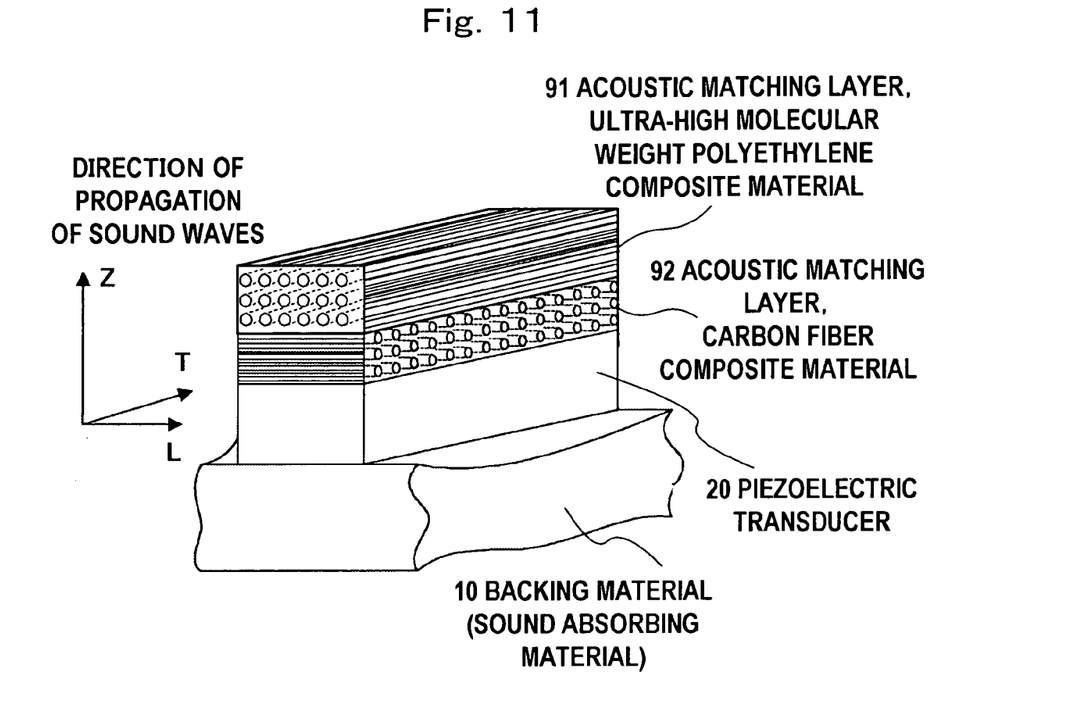
FIG. 11 is a view illustrating a fourth embodiment of the invention.

Next, described below in detail as a fourth embodiment is the structure of the probe using the composite material as the matching layers. Described below in detail is the structure of the probe using the composite material as the matching layers. FIG. 11 illustrates a transducer in this probe. A fibrous material is contained in the two matching layers. What makes a difference from the first, second and third embodiments is that the directions of fibers of the fibrous materials in the matching layers 91 and 92 are different from each other. In this embodiment, the directions of fibers in the two matching layers are differed from each other enabling the strength to increase in both the short-axis direction and in the lengthwise direction depending upon the layers.

What is common in these embodiments is that the direction of fibers of the fibrous material in the matching layers is perpendicular to the direction of propagation of sound waves. It is therefore allowed to decrease the sound waves propagating in a direction perpendicular to the direction of propagation of sound waves and to decrease the vibration in the transverse direction.

In the foregoing were described a plurality of acoustic matching layers all containing the fibrous material. However, the fibrous material may be contained in only either one of the acoustic matching layers. Further, through the plurality of acoustic matching layers were described above, only one acoustic matching layer may be applied to the probe.

Figure 12:
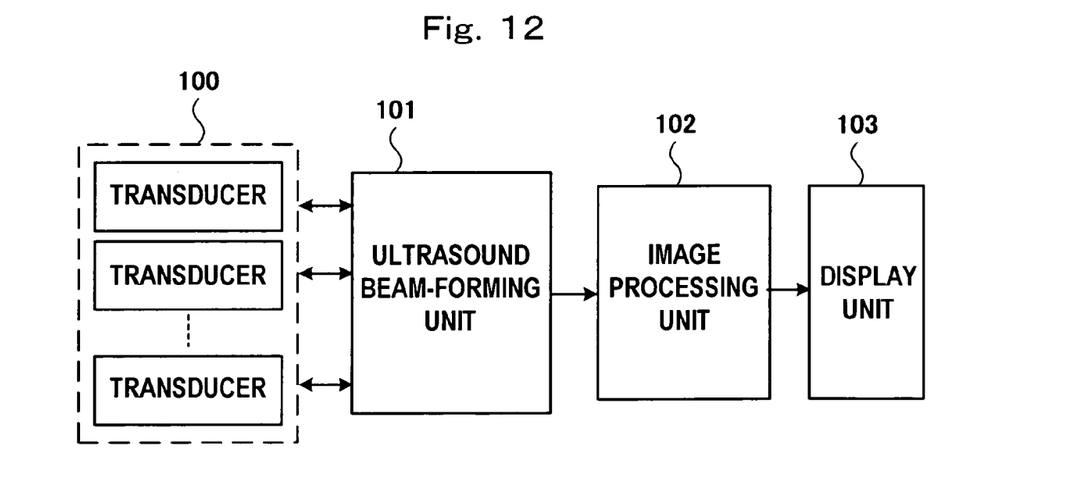
FIG. 12 is a diagram illustrating an ultrasonic apparatus as a whole.

FIG. 12 is a block diagram illustrating the whole constitution of the ultrasonic diagnostic apparatus using the ultrasound probe constituted according to the invention. Namely, the ultrasonic diagnostic apparatus comprises an ultrasound probe 100 for transmitting ultrasonic waves to, and receiving ultrasonic waves from, a sample, an ultrasonic beam-forming unit 101 which drives the ultrasound probe 100 to transmit ultrasonic waves and processes the reflected echo signals received by the ultrasound probe 100 to form an ultrasonic beam, an image processing unit 102 that receives signals from the ultrasonic beam-forming unit 101 and constitutes an ultrasonic image, and a display unit 103 that receives image signals from the image processing unit 102 to display an image, wherein the ultrasound probe 100 is the one in which there are provided the transducers of any one of FIGS. 5, 9, 10 and 11. In this case, the conversion efficiency is improved in the direction of thickness, and the vibration in the direction of width is prevented from interfering with the vibration in the direction of thickness realizing an ultrasonic diagnostic apparatus featuring improved image quality.

The invention claimed is:

1. An ultrasound probe comprising, on a backing, an acoustic lens, a plurality of transducers each of which comprises a piezoelectric transducer, and an acoustic matching layer provided between said piezoelectric transducer and said acoustic lens, wherein said acoustic matching layer contains a fibrous material, and a direction of fibers in said fibrous material is perpendicular to a direction of sound waves.

2. An ultrasound probe according to claim 1, wherein the direction of fibers in said fibrous material is perpendicular to the lengthwise direction of said transducer.

3. An ultrasonic probe according to claim 1, wherein the direction of fibers in said fibrous material is in parallel with the lengthwise direction of said transducer.

4. An ultrasound probe according to claim 1, wherein the direction of fibers in said fibrous material is aslant in the lengthwise direction of said transducer.

5. An ultrasound probe according to claim 1, wherein the Young's modulus of said fibrous material in the direction of fibers is greater than the Young's modulus of a mother member in said acoustic matching layer.

6. An ultrasound probe according to claim 1, wherein said acoustic matching layer comprises a first acoustic matching layer joined to said acoustic lens and a second acoustic matching layer provided between said first acoustic matching layer and said backing material.

7. An ultrasound probe according to claim 6, wherein the direction of fibers in the fibrous material of said first acoustic matching layer and the direction of fibers in the fibrous material of said second acoustic matching layer are perpendicular to each other.

8. An ultrasound probe according to claim 6, wherein the acoustic impedance of said first acoustic matching layer is lower than the acoustic impedance of said second acoustic matching layer.

9. An ultrasound probe according to claim 6, wherein said first acoustic matching layer is a polyethylene composite material, and said second acoustic matching layer is a carbon fiber composite material.

10. An ultrasound diagnostic equipment comprising an ultrasound probe of claim 1, an ultrasonic beam-forming unit which drives said ultrasound probe to transmit ultrasonic waves and processes the reflected echo signals received by said ultrasound probe to form an ultrasonic beam, an image processing unit that receives signals from said ultrasonic beam-forming unit and constitutes an ultrasonic image, and a display unit that receives image signals from said image processing unit to display an image.

11. An ultrasound probe according to claim 1, wherein said acoustic matching layer is constituted of an ortho-anisotropic material.

12. An ultrasound probe according to claim 1, wherein said acoustic matching layer enables the acoustic impedance in the direction of propagation of sound waves to be matched.

13. An ultrasound probe according to claim 1, wherein said acoustic matching layer is deformed mainly in the direction of thickness, thereby improving the conversion efficiency in the direction of thickness.

14. An ultrasound probe according to claim 1, wherein said acoustic matching layer enables sound evenly propagating in a direction perpendicular to the direction of travel not to be coupled by vibration in a transverse direction to the transducer.

* * * * *